United States Patent [19]

Ishizaki et al.

[11] Patent Number: 5,274,146
[45] Date of Patent: Dec. 28, 1993

[54] WATER-SOLUBLE ALKALI METAL SULFONATE-SUBSTITUTED BINAPHTHYLPHOSPHINE TRANSITION METAL COMPLEX AND ENANTIOSELECTIVE HYDROGENATION METHOD USING IT

[75] Inventors: Takerou Ishizaki; Hidenori Kumobayashi, both of Tokyo, Japan

[73] Assignee: Takasago International Corporation, Tokyo, Japan

[21] Appl. No.: 977,638

[22] Filed: Nov. 17, 1992

[30] Foreign Application Priority Data

Nov. 21, 1991 [JP] Japan .................. 3-331535

[51] Int. Cl.$^5$ .......................... C07F 9/02; C07F 15/00
[52] U.S. Cl. ...................... 556/14; 556/19; 556/136
[58] Field of Search ............ 556/136, 13, 14, 19, 556/20, 23, 18

[56] References Cited

U.S. PATENT DOCUMENTS

| | | | |
|---|---|---|---|
| 4,691,037 | 9/1987 | Yoshikawa et al. | 556/18 |
| 4,766,227 | 8/1988 | Sayo et al. | 556/23 X |
| 4,954,644 | 9/1990 | Sayo et al. | 556/14 |
| 4,994,590 | 2/1991 | Takaya et al. | 556/23 X |
| 5,159,093 | 10/1992 | Taketomi et al. | 556/136 |
| 5,210,243 | 5/1993 | Kolich | 556/136 X |

FOREIGN PATENT DOCUMENTS

| | | |
|---|---|---|
| 0245959 | 11/1987 | European Pat. Off. . |
| 0272787 | 6/1988 | European Pat. Off. . |
| 0372313 | 6/1990 | European Pat. Off. . |

*Primary Examiner*—Arthur C. Prescott
*Attorney, Agent, or Firm*—Sughrue, Mion, Zinn Macpeak & Seas

[57] ABSTRACT

An alkali metal sulfonate-substituted binaphthyl-phosphine transition metal complex is disclosed, which is represented by formula (I)

$$[M(X)_n(Q)(SO_3A\text{-}BINAP)]Y \quad (I)$$

wherein
M represents a transition metal atom;
$SO_3A$-BINAP represents a tertiary phosphine represented by formula (II)

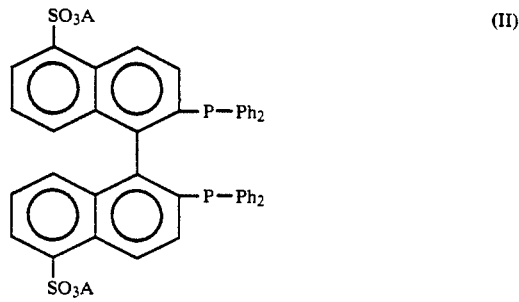

in which A represents an alkali metal atom;
X represents a chlorine atom, a bromine atom, or an iodine atom;
when n is 1, M represents ruthenium, Q represents benzene or p-cymene, and Y represents a chlorine atom, a bromine atom, or an iodine atom;
when n is 0 and M is iridium or rhodium, Q represents 1,5-cyclo-octadiene or norbornadiene, and Y represents $ClO_4$, $PF_6$ or $BF_4$; and
when n is 0 and M is palladium, Q represents $\pi$-allyl, and Y represents $ClO_4$, $PF_6$, or $BF_4$. A method of enantioselectively hydrogenating an olefin, a ketone, or an imine, which comprises carrying out the enantioselective hydrogenation using as a catalyst the alkali metal sulfonate-substituted binaphthylphosphine transition metal complex represented by formula (I) is also disclosed.

1 Claim, No Drawings

WATER-SOLUBLE ALKALI METAL SULFONATE-SUBSTITUTED BINAPHTHYLPHOSPHINE TRANSITION METAL COMPLEX AND ENANTIOSELECTIVE HYDROGENATION METHOD USING IT

FIELD OF THE INVENTION

The present invention relates to an enantioselective hydrogenation catalyst having a solubility in water and more particularly to a complex of a transition metal such as ruthenium, rhodium, iridium, palladium, etc., and a water-soluble phosphine compound. In another aspect, the present invention further relates to a method of enantioselectively hydrogenating an olefin, a ketone, or an imine using a catalyst having solubility in water.

BACKGROUND OF THE INVENTION

Hitherto, many reports have been reported about transition metal complexes utilizable for organic synthesis reactions, for example, about catalysts being used for enantioselective synthesis reactions such as an enantioselective hydrogenation reaction, an enantioselective isomerization reaction, an enantioselective silylation reaction, etc. In these complexes, many of the complexes obtained by coordinating an optically active tertiary phosphine compound to transition metals such as rhodium, palladium, ruthenium, iridium, nickel, etc., have an excellent performance as a catalyst for an enantioselective synthesis reaction and for further increasing the performance of the catalysts, many phosphine compounds having specific structures have been developed as described, e.g., in *Kagaku Sosetu* (*The Elements of Chemistry*) 32, "*Yuki Kinzoku Sakutai no Kagaku* (*Chemistry of Organometallic Complexes*", 237–238(1982), edited by The Chemical Society of Japan.

In particular, 2,2'-bis(diphenylphosphino)-1,1'-binaphthyl (hereinafter referred to as "BINAP") is one of excellent ligands and a rhodium complex using BINAP as the ligand (JP-A-55-61937) (the term "JP-A" as used herein means an "unexamined published Japanese patent application") and a ruthenium complex using BINAP as the ligand (JP-A-61-63690) have already been reported. Also, it has also been reported that a rhodium complex using 2,2'-bis[di(p-tolyl)phosphino]1,1'-binaphthyl (hereinafter referred to as "p-T-BINAP") as the ligand (JP-A-60-199898) and a ruthenium complex using p-T-BINAP as the ligand (JP-A-61-63690) give good results in an enantioselective hydrogenation reaction and an enantioselective isomerization reaction.

Furthermore, it has been reported that in an enantioselective hydrogenation reaction of nerol using as a catalyst a rhodium complex using 2,2'-bis(dicyclohexylphosphino)-1,1'-binaphthyl (hereinafter referred to as "CyBINAP"), citronellol having an optical purity of 66%ee was obtained [S. Inoue, et al., *Chemistry Letters*, 1007–1008(1985)].

As described above, for providing complexes having a higher performance as a catalyst for an enantioselective synthesis reaction, many specific phosphine compounds have been developed but according to the reactions and the substrates being used, these phosphine compounds are sometimes not yet sufficiently satisfactory in the point of the separation of the catalyst from the product formed and the reuse of the catalyst, and hence it has been desired to develop a complex which can be easily separated from the product formed as compared with conventional complexes (or catalysts).

SUMMARY OF THE INVENTION

As the result of the various investigations on many phosphine compounds for solving the foregoing theme, the inventors have discovered that a transition metal complex using as the ligand a novel phosphine compound having an alkali metal 5,5'-sulfonate binaphthyl group in place of the binaphthyl group of BINAP has a solubility in water, can be easily separated from the product formed, and enables the reuse of the catalyst, and have succeeded in accomplishing the present invention based on the discovery.

According to the present invention, there is provided a novel transition metal complex using as the ligand a dialkali metal 2,2'-bis(diphenylphosphino)-1,1'-binaphthyl-5,5'-disulfonate (hereinafter referred to as "SO$_3$A-BINAP") represented by formula (II)

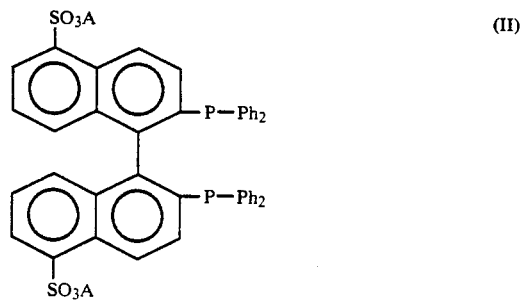

(II)

wherein A represents an alkali metal atom such as Na, K, etc.

That is, the present invention relates to an alkali metal sulfonate-substituted binaphthyl-phosphine transition metal complex represented by formula (I)

$$[M(X)_n(Q)(SO_3A\text{-}BINAP)]Y \qquad (I)$$

wherein

M represents a transition metal atom;

SO$_3$A-BINAP represents a tertiary phosphine represented by formula (II)

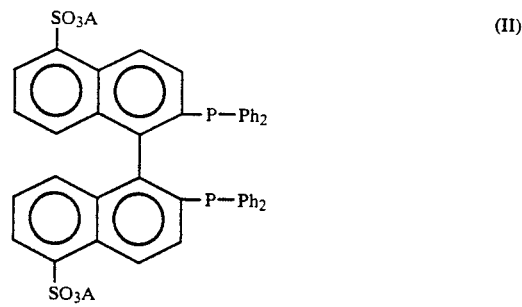

(II)

in which A represents an alkali metal atom;

X represents a chlorine atom, a bromine atom, or an iodine atom;

when n is 1, M represents ruthenium, Q represents benzene or p-cymene, and Y represents a chlorine atom, a bromine atom, or an iodine atom;

when n is 0 and M is iridium or rhodium, Q represents 1,5-cyclo-octadiene or norbornadiene, and Y represents ClO$_4$, PF$_6$ or BF$_4$; and when n is 0 and M is palladium, Q represents π-allyl, and Y represents $ClO_4$, $PF_6$, or $BF_4$.

The present invention further relates to a method of enantioselectively hydrogenating an olefin, a ketone, or an imine, which comprises carrying out the enantioselective hydrogenation using as a catalyst the alkali metal sulfonate-substituted binaphthylphosphine transition metal complex represented by formula (I) described above.

DETAILED DESCRIPTION OF THE INVENTION

Then, the present invention is described in detail.

$SO_3A$-BINAP for use in the present invention includes optically active isomers, the (+)-isomer and the (−)-isomer, and any of the (+)-isomer and (−)-isomer is included within the scope of the present invention.

In the present invention, $SO_3A$-BINAP forms a complex with a transition metal as the ligand. As the transition metal forming the complex, there are rhodium, iridium, palladium, ruthenium, etc.

Specific examples of the complex of the present invention are set forth below, in which COD means 1,5-cyclooctadiene, NBD means norbonadiene, and $\eta^3$-$C_3H_5$ means a π-allyl group. (These abbreviation apply to the following description.)

[Rh(COD)($SO_3A$-BINAP)]$ClO_4$

[Rh(NBD)($SO_3A$-BINAP)]$ClO_4$

[Rh(COD)($SO_3A$-BINAP)]$BF_4$

[Rh(NBD)($SO_3A$-BINAP)]$BF_4$

[Rh(COD)($SO_3A$-BINAP)]$PF_6$

[Rh(NBD)($SO_3A$-BINAP)]$PF_6$

[Ir(COD)($SO_3A$-BINAP)]$ClO_4$

[Ir(COD)($SO_3A$-BINAP)]$BF_4$

[Ir(COD)($SO_3A$-BINAP)]$PF_6$

[Ir(NBD)($SO_3A$-BINAP)]$ClO_4$

[Ir(NBD)($SO_3A$-BINAP)]$BF_4$

[Ir(NBD)($SO_3A$-BINAP)]$PF_6$

[Pd($\eta^3$-$C_3H_5$)($SO_3A$-BINAP)]$ClO_4$

[Pd($\eta_3$-$C_3H_5$)($SO_3A$-BINAP)]$BF_4$

[Pd($\eta^3$-$C_3H_5$)($SO_3A$-BINAP)]$PF_6$

[RuI(p-Cymene)($SO_3A$-BINAP)]I

[RuBr(p-Cymene)($SO_3A$-BINAP)]Br

[RuCl(p-Cymene)($SO_3A$-BINAP)]Cl

[RuI($C_6H_6$)($SO_3A$-BINAP)]I

[RuBr($C_6H_6$)($SO_3A$-BINAP)]Br

[RuCl($C_6H_6$)($SO_3A$-BINAP)]Cl

As a method of producing the transition metal complex of the present invention, there is the same method as the synthesis method of [Rh(COD)(dppe)]$ClO_4$ [wherein dppe means 1,2-bis(diphenylphosphino)ethane] reported, e.g., in J. A. Osborn et al., *Journal of American Chemical Society*, 93, 2397(1971). That is, after reacting [Rh(COD)$_2$]$ClO_4$ as a raw material and $SO_3A$-BINAP in a solvent such as methanol, ethanol, water, etc., singly or in a mixture of these solvents at room temperature from 30 minutes to overnight, by distilling off the solvent(s) under a reduced pressure, [Rh(COD)($SO_3A$-BINAP)]$ClO_4$ can be quantitatively synthesized.

Also, as the synthesis method of [Ir(COD)(dppe)]$BF_4$ reported in M. Green et al., *Journal of Chemical Society*, (A), 2334(1971), after reacting [Ir(COD)($CH_3CN$)$_2$]$BF_4$ as a raw material and $SO_3A$-BINAP in a solvent such as methanol, ethanol, water, etc., singly or in a mixture of these solvents at room temperature from 30 minutes to overnight, by distilling off the solvent(s) under a reduced pressure, [Ir(COD)($SO_3A$-BINAP)]$BF_4$ can be quantitatively synthesized.

Furthermore, as the synthesis method of [Pd($\eta^3$-$C_3H_5$)(dppe)]$ClO_4$ reported in Ootuka et al., *Chemistry Letter*, 157(1986), by reacting [Pd($\eta_3$-$C_3H_5$)Cl]$_2$ as a raw material and $SO_3A$-BINAP in a mixture solvent of water and methanol in the presence of $NaClO_4$, [Pd($\eta^3$-$C_3H_5$)($SO_3A$-BINAP)]$ClO_4$ can be synthesized.

Moreover, as the synthesis method of [RuI(p-Cymene)(BINAP)]I reported in Takaya et al., *Journal of Chemical Society, Chemical Communication*, 609(1991), after reacting [RuI$_2$(p-Cymene)]$_2$ as a raw material and $SO_3$ A-BINAP in methanol solvent at room temperature from 30 minutes to overnight, by distilling off the solvent under a reduced pressure, [RuI(p-Cymene)($SO_3A$-BINAP)]I can be quantitatively analyzed.

When the transition metal complex thus obtained is used as a catalyst for an enantioselective synthesis reaction such as, for example, the enantioselective hydrogenation reaction of an olefin, a ketone, and an imine, the reaction can be carried out in an aqueous solution and also the reaction is carried out in an ordinary organic solvent and after transferring the catalyst into an aqueous layer, the catalyst can be easily separated from the hydrogenation product.

Also, when one of the (+)-isomer and (−)-isomer of $SO_3A$-BINAP in the present invention is selected and the transition metal complex using it as the ligand is used as a catalyst, the desired product of the absolute configuration can be obtained in an enantioselective synthesis reaction.

Then, the following examples are intended to illustrate in more detail but not to limit the invention any way.

In addition, the measurements in the examples were carried out using the following instruments.

NMR: AM-400 Type Apparatus (400 MHz) (manufactured by Bruker Inc.). Internal standard substance: $^1$H-NMR . . . tetramethylsilane. External standard substance: $^{31}$P-NMR . . . 85% phosphoric acid.

Optical Rotation DIP-4 Type Apparatus (manufactured by JASCO Inc.).

Optical Purity: High-Performance Liquid Chromatography L-6000 (manufactured by Hitachi, Ltd.) Detector: UV Detector L-4000UV (manufactured by Hitachi, Ltd.).

Chemical Purity: High-Performance Liquid Chromatography L-6000 (manufactured by Hitachi, Ltd.) Detector: UV Detector L-4000UV (manufactured by Hitachi, Ltd.).

Elemental Analysis: CHN 2400 (manufactured by Perkin-Elmer Co.).

Chemical Purity: Gas Chromatography (manufactured by Hewlett Packard Ltd.) Column HP-1 0.25 mm$\phi$×25 m.

Chemical Purity: Gas Chromatography GC-9A (manufactured by Shimazu Corporation)
Column: PEG-HT 0.25 mm$\phi$×25 m.

EXAMPLE 1

Synthesis of sodium (+)-2,2'-bis(diphenylphosphino)-1,1'-binaphthyl-5,5'-disulfonate [(+)-SO$_3$Na-BINAP]

To 20 ml of 95% $H_2SO_4$ was slowly added dropwise 40 ml of 30% $SO_3$—$H_2SO_4$.

To the solution was added 10 g (16 mmols) of (+)-BINAP, the temperature of the mixture was gradually raised to 40° C. with stirring, and the mixture was further stirred for 2 hours at the same temperature. Then, the reaction mixture obtained was added dropwise to an aqueous NaOH solution (94 g of NaOH and 360 ml of water) under water cooling. Precipitates thus formed were recovered by filtration, washed with water, and dried under a reduced pressure. To the solids obtained was added 2 liters of ethanol followed by refluxing for one hour by heating, thereafter, insoluble matters were filtered off, and the filtrate was concentrated to dryness. The solids obtained were recrystalized from 200 ml of ethanol to provide 4.88 g of sodium (+)-2,2'-bis(diphenylphosphino)-1,1'-binaphthyl-5,5'-disulfonate. The percent yield thereof was 37%.

Melting point > 300° C.

$^1$H-NMR(CD$_3$OD) $\delta$:
6.76–7.26 (m, 24H), 7.47–7.50 (m, 2H), 7.98–8.00 (m, 2H), 8.92–8.94 (m, 2H).

$^{31}$P-NMR (CD$_3$OD) $\delta$: −15.8 (S).

$[\alpha]_D^{25} = +3.06°$ (C 0.45 CH$_3$OH).

Elemental Analysis for C$_{44}$H$_{30}$O$_6$S$_2$Na$_2$(H$_2$O)$_5$: Calculated: C:57.64, H:4.40. Found: C:58.05, H:4.13.

EXAMPLE 2

In a 50 milli-liter flask with side arm were placed 0.1023 g (1.05×10$^{-4}$ mol) of [RuI$_2$(p-Cymene)$_2$]$_n$ synthesized by the method described in Mashima et al., *Journal of Chemical Society, Chem. Commun.*, 1208(1989) and 0.2001 g (2.42×10$^{-4}$ mol) of (+)-SO$_3$Na-BINAP obtained in Example 1 and after displacing the atmosphere in the flask with a nitrogen gas, 5 ml of methanol was added to the mixture followed by stirring for 15 hours at room temperature. After filtering off insoluble matters with celite, methanol was distilled off from the filtrate and the residue formed was dried under a reduced pressure to provide 0.29 g of iodo-$\pi$-p-Cymene[sodium 2,2'-bis(diphenylphosphino)-1,1'-binaphthyl-5,5'-disulfonate]ruthenium iodide[RuI(p-Cymene)((+)-SO$_3$Na-BINAP)]I. The yield was quantitative.

$^{31}$P-NMR (CD$_3$OD) $\delta$: 25.15 (d,J=59.74 Hz), 40.71 (d,J=59.35 Hz).

Elemental Analysis for C$_{54}$H$_{44}$O$_6$S$_2$P$_2$Na$_2$I$_2$Ru: Calculated: C:49.30, H:3.37. Found: C:48.74, H:3.51.

Solubility in Water: 0.8% by weight.

EXAMPLE 3

In a 50 milli-liter flask with side arm were placed 0.28 g (5.97×10$^{-4}$ mol) of [Ir(COD)(CH$_3$CN)$_2$]BF$_4$ synthesized by the method described in M. Green et al., *Journal of Chemical Society*, (A), 2334(1971) and 0.50 g (6.05×10$^{-4}$ mol) of (+)-SO$_3$Na-BINAP obtained in Example 1 and after displacing the atmosphere in the flask with a nitrogen gas, 10 ml of methanol and 5 ml of water were added to the mixture followed by stirring for 15 hours at room temperature. After filtering off insoluble matters with celite, the solvents were distilled off from the filtrate and the residue was dried at a reduced pressure to provide 0.76 g of 1,5-cyclooctadiene-[sodium 2,2'- bis(diphenylphosphino)-1,1'-binaphthyl-5,5'-disulfonate]iridium tetrafluoroborate[Ir(COD)-((+)-SO$_3$Na-BINAP)]BF$_4$. The yield was quantitative.

$^{31}$P-NMR(CD$_3$OD) $\delta$: 16.04 (S).

Elemental Analysis for C$_{52}$H$_{42}$O$_6$S$_2$P$_2$Na$_2$BF$_4$Ir(H$_2$O)$_5$: Calculated: C:47.89, H:4.02. Found C:48.13, H:3.96.

Solubility in water: 0.1% by weight.

EXAMPLE 4

In a 50 milli-liter flask with side arm were placed 0.21 g (5.51×10$^{-4}$ mol) of [Rh(C$_7$H$_8$)$_2$]ClO$_4$ synthesized by the method described in T. G. Schenck et al., *Inorganic Chemistry*, 2334(1985) and 0.50 g (6.05×10$^{-4}$ mol) of (+)-SO$_3$Na-BINAP obtained in Example 1 and after displacing the atmosphere in the flask with a nitrogen gas, 10 ml of methanol and 3 ml of water were added to the mixture followed by stirring for 15 hours. Then, after filtering off insoluble matters with celite, the solvents were distilled off from the filtrate and the residue was dried at a reduced pressure to provide 0.57 g of bicyclo[2,2,1]hepta-2,5-diene-[sodium 2,2'-bis(diphenylphosphino)-1,1'-binaphthyl-5,5'-disulfonate]rhodium perchlorate [Rh(C$_7$H$_8$)((+)-SO$_3$Na-BINAP)]ClO$_4$. The percent yield was 93%.

$^{31}$P-NMR(CD$_3$OD) $\delta$: 26.29 (d,J=78.04 Hz).

Elemental Analysis for C$_{51}$H$_{38}$O$_{10}$S$_2$P$_2$Na$_2$ClRh(H$_2$O)$_7$: Calculated: C:49.08, H:4.20. Found: C:48.75, H:4.03.

Solubility in Water: 0.4% by weight.

APPLICATION EXAMPLE 1

Enantioselective Hydrogenation Reaction of Ethyl Acetoacetate

Under a nitrogen gas atmosphere, 0.0096 g (7.3×10$^{-6}$ mol) of [RuI(p-Cymene)((+)-SO$_3$Na-BINAP)]I, 0.1164 g (7.8×10$^{-4}$ mol) of NaI, 1 ml (7.5×10$^{-3}$ mol) of ethyl acetoacetate, and 1.5 ml of water were charged in a 100 milli-liter autoclave. After displacing the inside atmosphere of the autoclave with a hydrogen gas, the autoclave was pressed at a hydrogen pressure of 50 kg/cm$^2$ and the mixture was stirred for 40 hours at 65° C. After the reaction was over, the hydrogen gas was removed, and after added thereto 100 ml of water and 100 ml of ether, the ether extraction was carried out. The ether extract was recovered, dried with anhydrous sodium sulfate, and further ether was distilled off to provide 0.62 g (percent yield 63%) of ethyl 3-hydroxybutyrate. By the analysis of gas chromatography (PEG-HT), the conversion ratio was determined to be 99%.

Also, to a mixture of 0.0542 g (4.81×10$^{-4}$ mol), 0.10 g (4.27×10$^{-4}$ mol) of (R)-(+)-$\alpha$-methoxy-$\alpha$-trifluoromethylphenyl-acetic acid (MTPA), 0.0891 g (4.31×10$^{-4}$ mol) of N,N'-dicyclo-hexylcarbodiimide, and a small amount of 4-dimethylaminopyridine was added 5 ml of methylene chloride, after stirring the mixture for 3 hours at room temperature, the solvent was distilled off. Then, 5 ml of ether was added to the solid residue formed and the dissolved portion was recovered to provide the MTPA ester of ethyl (—)-3-hydroxybutyrate.

By a diastereomer ratio analysis with gas chromatography (PEG-HT), the optical yield of ethyl (—)-3-hydroxybutyrate was determined to be 91%ee.

Also, after the reaction was over, the reaction mixture was extracted twice with 200 ml of toluene under a nitrogen gas stream, after recovering ethyl 3-hydroxybutyrate as the product, 1 ml of ethyl acetoacetate was added again to the aqueous layer and the hydrogenation was carried out under the same condition as above, thereby the same result as above could be obtained. That is, it can be seen that the complex of this invention can be utilized as an excellent catalyst which can be repeatedly used.

APPLICATION EXAMPLE 2

Enantioselective Hydrogenation Reaction of Acetophenonebenzylimine (1) Under a nitrogen gas atmosphere, to a mixture of 0.014 g ($2.1 \times 10^{-5}$ mol) of [Ir(COD)Cl]$_2$ and 0.036 g ($4.4 \times 10^{-5}$ mol) of (+)-SO$_3$Na-BINAP was added 3 ml of methanol and the resultant mixture was stirred for one hour at room temperature to obtain a mixture Ir(COD)((+)-SO$_3$Na-BINAP)Cl.

(2) Under a nitrogen gas atmosphere, the mixture obtained in above step (1), 0.91 g ($4.4 \times 10^{-3}$ mol) of acetophenonebenzylimine, and 2 ml of methanol were charged in a 100 milli-liter autoclave. After displacing the inside atmosphere of the autoclave with a hydrogen gas, the autoclave was pressed at a hydrogen pressure of 50 kg/cm$^2$ and the mixture was stirred for 12 hours at room temperature. After the reaction was over, the hydrogen gas was removed and after distilling off methanol from the reaction mixture, 100 ml of an aqueous sodium hydroxide solution of 1 mol concentration and 100 ml of ether were added to the residue to carry out the extraction of the product formed into the ether layer. After separating the organic layer (ether layer) from the aqueous layer, the organic layer was dried with anhydrous sodium sulfate and then the solvent was distilled off to provide 0.64 g (percent yield 70%) of N-benzyl-α-phenethylamine.

By a gas chromatographic analysis, the conversion ratio was determined to be 99% and the selectivity was 90%.

Also, after distilling the product, the optical rotation was measured and in this case, $[\alpha]_D^{25}$ was $-22.78°$ (C=1.17 ethanol).

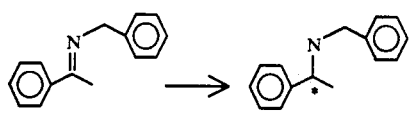

APPLICATION EXAMPLE 3

Enantioselective Hydrogenation Reaction of Aminomethyl Phenyl Ketone

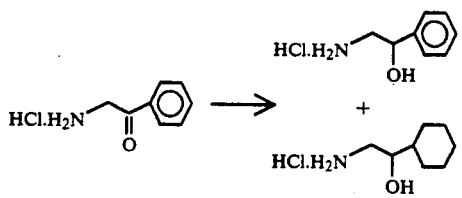

Under a nitrogen gas atmosphere, 0.20 g ($1.2 \times 10^{-3}$ mol) of aminomethyl phenyl ketone hydrochloride, 0.0042 g ($3.9 \times 10^{-6}$ mol) of a catalyst, Rh(COD)((+)-SO$_3$Na-BINAP)Cl formed by mixing [Rh(COD)Cl]$_2$ and (+)-SO$_3$Na-BINAP, and 5 ml of water were charged in a 100 milli-liter autoclave. After displacing the inside atmosphere of the autoclave with a hydrogen gas, the autoclave was pressed at a hydrogen pressure of 30 kg/cm$^2$ and the mixture was stirred for 64 hours at room temperature. After the reaction was over, the hydrogen gas was removed, precipitates formed were filtered, and 100 ml of an aqueous sodium hydroxide solution of 1 mol concentration and 100 ml of ether were added to the filtrate to extract the product into the ether layer. After separating the organic layer (ether layer) from the aqueous layer, the organic layer was dried with anhydrous sodium sulfate and then the solvent was distilled off to provide 0.09 g of a mixture of 2-amino-1-phenyl ethanol and 2-amino-1-cyclohexyl ethanol.

By analyzing the reaction mixture obtained with high-performance liquid chromatography and gas chromatography, it was confirmed that the conversion ratio was 18% and the ratio of 2-amino-1-phenyl ethanol to 2-amino-1-cyclohexyl ethanol was 1:1.

The mixture was separated and purified by a silica gel column (chloroform/methanol=5/1) and the optical rotation of 2-amino-1-phenyl ethanol was measured.

In this case, $[\alpha]_D^{25}$ was $+8.54°$ (C=0.11, ethanol).

HPLC Condition

Column: Cosmosil 5Ph (trade name, manufactured by Nacalai Tesque, Inc., 4.6 mm×250 mm).

Transfer Phase: 0.05M NaH$_2$PO$_4$ (pH 2.4).

Flow Rate: 1.0 ml/min.

Wavelength: 210 nm.

As described above, the water-soluble alkali metal sulfonate-substituted binaphthylphosphine compounds of the present invention form complexes with a transition metal such as rhodium, ruthenium, iridium, palladium, etc., and the complexes can be used as very important catalysts for various enantioselective synthesis reactions. Thus, the foregoing compounds of the present invention have high industrially utilizable values.

While the invention has been described in detail and with reference to specific embodiments thereof, it will be apparent to one skilled in the art that various changes and modifications can be made therein without departing from the spirit and scope thereof.

What is claimed is:

1. An alkali metal sulfonate-substituted binaphthylphosphine transition metal complex represented by formula (I)

$$[M(X)_n(Q)(SO_3A\text{-}BINAP)]Y \qquad (I)$$

wherein

M represents a transition metal atom;

SO₃A-BINAP represents a tertiary phosphine represented by formula (II)

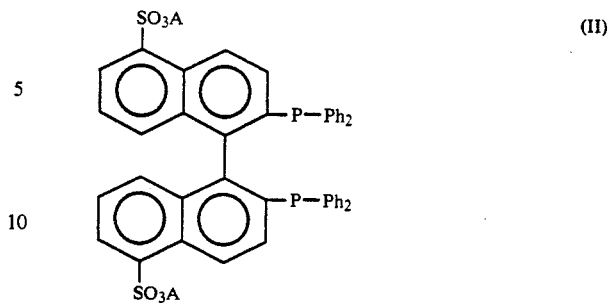

in which A represents an alkali metal atom;
X represents a chlorine atom, a bromine atom, or an iodine atom;
when n is 1, M represents ruthenium, Q represents benzene or p-cymene, and Y represents a chlorine atom, a bromine atom, or an iodine atom;
when n is 0 and M is iridium or rhodium, Q represents 1,5-cyclo-octadiene or norbornadiene, and Y represents ClO₄, PF₆ or BF₄; and
when n is 0 and M is palladium, Q represent π-allyl, and Y represents ClO₄, PF₆, or BF₄.

* * * * *